United States Patent

Whalen et al.

[11] Patent Number: 5,464,471
[45] Date of Patent: Nov. 7, 1995

[54] FIBRIN MONOMER BASED TISSUE ADHESIVE

[75] Inventors: Robert L. Whalen, Somerville; Donald Dempsey, Newbury, both of Mass.

[73] Assignee: Whalen Biomedical Inc., Somerville, Mass.

[21] Appl. No.: 339,176

[22] Filed: Nov. 10, 1994

[51] Int. Cl.$^6$ ............................................. C09J 189/00
[52] U.S. Cl. ........................ 106/124; 604/290; 514/12
[58] Field of Search ........................ 106/124; 606/214; 604/290; 514/12

[56] References Cited

U.S. PATENT DOCUMENTS

| | | | |
|---|---|---|---|
| 3,969,240 | 7/1976 | Kolobow et al. | 210/321 |
| 4,362,567 | 7/1982 | Schwarz et al. | 106/157 |
| 4,414,976 | 11/1983 | Schwarz et al. | 106/161 |
| 4,735,616 | 4/1988 | Eibl et al. | 606/191 |
| 4,909,251 | 3/1990 | Seelich | 606/213 |
| 5,219,895 | 6/1993 | Kelman et al. | 522/68 |
| 5,330,974 | 7/1994 | Pines et al. | 514/21 |

*Primary Examiner*—David Brunsman

[57] ABSTRACT

A single agent fibrin based hemostatic and tissue adhesive agent comprised of recombinant fibrin monomer, Bovine thrombin, and calcium chloride, which is lyophilized to powder form, and is activated upon blood contact, at the site of tissue injury, producing effective hemostasis and subsequent tissue adhesion.

7 Claims, No Drawings

FIBRIN MONOMER BASED TISSUE ADHESIVE

LICENSE RIGHTS

The U.S. government has a paid up license in this invention and the right, in limited circumstances to require the patent owner to license others on reasonable terms as provided by U.S. Army contract number DAMD 12-94-C-4039.

BACKGROUND

1. Field of the Invention

This invention relates to a fibrin based tissue adhesives for achieving hemostasis.

2. Description of Prior Art

The ability to establish expeditious and permanent bonding between biological tissues is a critical factor in the success of many medical procedures, from surgical operations to wound dressings. Attempts to provide such bonding through mechanical means have proven inadequate. Consequently, biomedical research has focused on the development of natural and synthetic materials to act as adhesives, sealants and hemostatic agents. In connection with the description of previous inventions and the invention herein, the terms adhesive, sealant and hemostatic agent are defined broadly and used as these terms are understood in the art.

The clinical applications of such tissue adhesive agents are extensive and diverse. Aside from simple hemorrhage control and wound closure, applications include the treatment and preservation of the ruptured spleen (Brands, W. et al., World J. Surg., 6. 366–368, (1982)), the sealing of vascular prostheses (Walterbusch. G. et al., Thorac. cardiovasc. Surgeon, 30, 234–235, (1982)), the sealing of vascular grafts prior to implantation (Kalmer, P. et al., Thorac. cardiovasc. Surgeon, 30, 230–23 1, (1982)), the sealing of microvascular anastomoses (Pearl, RM et al., Surgery, Gynecology & Obstetrics, 144, 227–230, (1977)), the repair of middle ear defects (Epstein, GH et al., Ann Otol. Rhinol. Laryngol., 95, 40–45, (1986), and Silberstein. LE et al., Transfusion, 28(4), 319–321, (1988)), and the bonding of a corneal inlay into a recess prepared to receive same in the cornea of a patient. In fact, marketing research has indicated that there are over 8 million surgical procedures that could utilize a safe, effective biological adhesive.

Major interest in the use of synthetic polymeric materials to act as adhesives, sealants and hemostatic agents began in the early sixties. Initial work was confined to water-soluble systems such as casein and polyvinyl alcohol, but was later expanded to include all available synthetic adhesives and plastics with no known local or general toxicity. Although many materials were investigated, the most widely used tissue adhesives were the cyanoacrylates. These are a homologous series of organic molecules which polymerize and adhere to moist living tissues. Methyl-alpha-cyanoacrylate (MCA) in particular, has been used since 1960 by many investigators as a non-suture adhesive for bones. MCA is a fluid, monomeric material which polymerizes in seconds under mild pressure to produce a thin, strong, adherent film. However, these materials have been shown to be histotoxic and induce detrimental inflammatory tissue reaction.

Such toxicity with synthetic adhesives has led investigations toward the development of biologically derived bonding materials. These materials often consist of elements from the natural bonding mechanism, such as collagen or fibrin. Collagen is a major connective tissue protein which is evident in prior art of many biomedical products, such as an artificial cornea (U.S. Pat. No. 4,581,0303, a hemostatic agent (U.S. Pat. No. 4,2 15,2003 and a soft contact lens (U.S. Pat. Nos. 4,264,155: 4,264,493; 4,349,470; 4,388,428; 4,452,925 and 4,650,6163, due to its good biocompatibility. However, natural collagen must be modified to render it suitable for use as a biomedical adhesive.

In many instances, the prior modified collagen-based adhesives suffer from various deficiencies which include (1) crosslinking/polymerization reactions that generate exothermic heat, (2) long reaction times, and (3) reactions that are inoperative in the presence of oxygen and physiological pH ranges (Lee, ML et al., Adhesion in Biological Systems, RS Manly, ed., Academic Press, New York, 1970. Ch. 17) Moreover, many of these adhesives contain toxic materials rendering them unsuitable for biomedical use. As a result, recent processing developments have been revealed, as in U.S. Pat. No. 5,219,895 to Kelman, in which pure, soluble or partially fibrillar collagen monomers are chemically modified to be soluble at physiological conditions and polymerize to achieve sealant properties.

Improvements of this sort still have not produced an agent as effective in achieving hemostasis as fibrin based tissue adhesives. Compared with oxidized cellulose, microfibrillar collagen, or surface charge modified collagen, the use of fibrin adhesive results in significantly less blood loss at the site of injury (Raccuia, JS et al. Comparative efficacy of topical hemostatic agents in a rate kidney model. Am. J. Surg. 163(2):234–8, 1992). Consequently, tissue adhesives of this type have been developed as seen in U.S. Pat. Nos. 4,362,567 and 4,414,976 and Can. Pat. No. 1,168,982. The foundation of these agents are the proteins fibrinogen and thrombin.

Fibrinogen is a soluble protein found in the blood plasma of all vertebrates. When fibrinogen is contacted by thrombin, a protein enzyme, it is converted into fibrin monomer and Factor XIII is activated to Factor XIIIa. Factor XIIIa then polymerizes the fibrin monomer to form a stabilized fibrin network. Such a network is essential to the healing process of wound closure and tissue bonding. The network serves as a physical bond and as a scaffolding to support the migration of immunologically active cells, for defense against invading pathogens, and epithelial cells, for tissue regeneration and repair. The fibrin network may then be gradually dissolved by the body (fibrinolysis) after treatment leading to a more normal appearance of the healed site.

Tissue adhesive preparations of this type usually consist of a fibrinogen solution containing Factor XIII, some additional proteins, such as fibronectin and albumin, and active or nonactive additions. A thrombin solution may also be provided containing thrombin and calcium ions, or the thrombin may be provided from the tissue area to be bonded itself. These solutions are commercially available in the form of either deep-frozen solutions or lyophilisate due to their lack of stability as liquid aqueous solutions. Therefore, these products are typically packaged in the form of kits, which include the protein ingredients, means to prepare the solutions, and means to utilize the solutions.

In emergency situations, quick availability of the tissue adhesive may be of decisive importance. However, the use of these kits is often difficult, tedious and time consuming. These constraints pose a problem in the hospital setting and may be completely defeating in the field or combat settings. To overcome this, there have been attempts to shorten the preparation time. This usually involves shortening the reconstitution time of lyophilized solutions. For instance, Can. Pat. No. 1,182,444 describes a method and an arrangement for accelerating the dissolution of lyophilized medicines. The combined heating and stirring device disclosed markedly shortened reconstitution times, yet physicians have voiced a desire for further improvements.

It has been known that the solubility of hard-soluble proteins can be improved by certain additions. Thus, EP-A-0 085 923 discloses a lyophilized fibrinogen composition which additionally contains a further substance having a urea or guanidine residue. However, it has been shown that such additions have a cytotoxic effect, inhibit the growth of fibroblasts and cause the formation of an irregular fibrin structure resulting in the loss of desired elasticity of the fibrin. These effects jeopardize the desired properties of fibrinogen-based tissue adhesives, such as the stimulation of wound healing and the capacity for high strain.

Others, such as U.S. Pat. No. 4,909,251 to Seelich, utilize a biologically compatible tenside addition to the fibrinogen composition, and optionally further proteins as well as adjuvants or additives, to reduce reconstitution times. The tenside is from the group of non-ionic, cationic, anionic or zwitterionic tensides and is present in an amount from 0.03 to 15% by mass based on the fibrinogen content. Additions such as this have been shown to be useful in preparations having a high content of fibronectin, a plasma protein which is difficult to dissolve.

However, there are still existing inherent disadvantages to the present system of hemostatic and tissue adhesive compounds. The therapeutic compositions of some fibrin sealants and agents still contain non-autologous, non-single donor human fibrinogen, that is they comprise fibrinogen derived, or pooled from multiple human donors. Because of the risk of viral disease such as AIDS, hepatitis B and C, these compositions are not in use in the United States. With various incidents of infection reported it is unlikely that these compounds would ever be released for use in the United States.

Accordingly, practitioners of the art have sought to provide autologous or single donor fibrinogen compositions to minimize the risk of viral infection. However, substantial variation in the fibrinogen content of such preparations has lead to difficulty in predicting, accurately, the clinically effective dose required.

An alternate resolution to the above mentioned risks characteristic of human plasma derived therapeutic products was to provide fibrinogen from a mammalian source other than humans. This, however, can result in a severe immune response. Even the currently available highly purified bovine fibrinogen compositions, such as those indicated in U.S. Pat. No. 5,330,974, contain some foreign antigen.

A significant improvement in the design of fibrin tissue adhesives would involve the complete elimination of such solution preparation and mixing time, eliminate the risk of viral transmission, and severe immunologic response. A tissue adhesive of this type would consist of a blood activated single agent that is usable in a dry form, utilizing genetically engineered fibrin monomer, thus avoiding the time and constraints of preparing and pre-mixing ingredients, as well as any risk of viral transmission. The present invention provides such an agent. The new agent is distinguished from previously described fibrin tissue adhesives in that it is prepared using a genetically engineered fibrin monomer rather than fibrinogen. This allows it to be lyophilized from a single solution containing all of its constituents, including thrombin. Consequently, the agent is available as a dry powder which is activated upon blood contact producing effective hemostasis and subsequent adhesion.

Numerous publications describe the successful use of a simplified fibrin glue consisting of fibrinogen, thrombin, calcium chloride and Factor XIII (Kjaergard, HK et al., Ann Thorac Surg, 55(2):543–44, 1993; Hartman, AR et al., Arch Surg, 127:357–59, 1992; Dahlstrom, KK et al., Plastic and Reconstructive Surgery, 89(5):969–976, 1992). If one assumes that sufficient Factor XIII will be present in the blood being lost at the site of injury, it is possible to prepare a fibrin glue for hemorrhage control consisting of fibrinogen, thrombin and calcium chloride. One problem in preparing a solution with these ingredients, however, is the formation of a fibrin gel directly from the interaction of fibrinogen and thrombin. Therefore, a solution containing fibrin monomer is used instead of its precursor fibrinogen.

In the early stages of polymerization, the fibrin monomer molecules attach to each other by loose hydrogen and hydrophobic bonds which can be broken apart with ease. It is at this point that the fibrin monomer is utilized. The loosely bound monomers are chemically disrupted and the mixture is sonicated or shaken until the gel is dissolved. The dissolved fibrin monomer is then used to prepare a solution with thrombin and calcium chloride. This solution is finally lyophilized to dryness to provide a single agent fibrin tissue adhesive.

This method of preparation is necessary because it is not feasible to simply mix separately lyophilized powders in the correct proportions. The principal difficulty is in uniformly mixing the ingredients. The amount of thrombin, for example, is quite small compared to the amount of clottable protein: thus, it would be extremely difficult to thoroughly blend the two powders to achieve a consistent mixture. The method of the inventors produces a uniform preparation by virtue of being lyophilized from a true solution of its constituents.

When the lyophilized agent is exposed to Factor XIII, present in the blood at the site of use, the fibrin monomer will precipitate as stabilized fibrin with the appropriate adhesive qualities. The added thrombin, of course, also induces platelet aggregation which assists in achieving hemostasis.

The formulation of the single agent tissue adhesive may have additions, such as aprotinin, an inhibitor of fibrinolysis, or antibiotics. Likewise, numerous "inert" additives (substances such as preservatives, dispersants or additional diluents) known in the art can be added to the therapeutic compositions of the invention, with the understanding that such substances are physiologically compatible.

The therapeutic compositions and methods defined by the present invention are useful in connection with any of the clinical applications where adhesives, sealants and hemostatic agents can be used. Tissue adhesion, sealing of tissue or hemostasis are induced in a mammalian patient at a site of treatment by contacting the treatment site with a therapeutically effective amount of composition. According to the practice of the invention, such effective amounts need not be equivalent to amounts that cause complete or permanent adhesion of tissue, causing total sealing of tissue boundary or complete arrest of bleeding or loss of tissue fluid from a tissue or tissue boundary. Rather, such compositions are within the scope of the invention if the use thereof provides at least a partial effect that is of benefit to the patient in the course of treatment.

Amount of agent necessary to perform clinical procedures varies widely depending on, for example, the size of the treatment site, the nature of the condition in need of treatment and factors unique to each patient. It is accepted in the art that it is the skill of the clinical practitioners to determine for each patient and for each condition the amounts of the agent that are effective.

The lyophilized composition of the invention may be used directly in powder form by directly sprinkling the agent onto a wound site or surgical incision. As it reacts with the blood and tissue fluids at the site, it will effect a seal or hemostasis. This is typically useful when the site to be closed is small and blood loss is not rapid.

Additionally, the lyophilized composition may be applied to a wound or surgical incision by, for example, incorporation into a gauze pad, sponge, collagen or gel-type matrix or into a similar device in treating the area. This is useful in controlling bleeding due to deep tissue injury involving arterial blood loss. It may also be useful in the treatment of more superficial wounds in which external semi-occlusive dressings may be applied.

SUMMARY OF THE INVENTION

With the above in view, it is therefore among the primary objectives of this invention to provide a single agent fibrin based hemostatic and tissue adhesive agent comprised of recombinant fibrin monomer, Bovine thrombin, and Calcium Chloride, which is lyophilized to powder form, and is activated upon blood contact, at the site of tissue injury, producing effective hemostasis and subsequent tissue adhesion.

It is another object of the present invention to provide a hemostatic agent/tissue adhesive which utilizes a recombinant fibrin monomer thus eliminating the risk of pooled human plasma derived fibrin, as well as eliminating severe immunologic reactions to pooled mammalian derived fibrin.

It is still another object of the invention to provide a fibrin monomer hemostatic agent/tissue adhesive which can be applied directly to the site of injury, in powdered form, without reconstitution.

It is yet another object of the invention to provide a therapeutic single agent fibrin monomer tissue adhesive, tissue sealant, or hemostatic agent derived from the thrombin-fibrinogen polymerization reaction.

DETAILED DESCRIPTION OF THE INVENTION

This invention provides for a lyophilized fibrin monomer containing therapeutic composition effective as a tissue adhesive, tissue sealant, or hemostatic agent. A therapeutic single agent fibrin monomer tissue adhesive is derived from the thrombin-fibrinogen polymerization reaction, which is then prevented from stabilizing.

Due to the structure of the coagulation cascade, the fibrin monomer may be obtained in vitro by a variety of approaches. First, it is known that fibrin monomer is formed when the protein enzyme, thrombin, acts on the protein fibrinogen. With its proteolytic capabilities, thrombin removes two low molecular weight peptides from each molecule of fibrinogen, forming a molecule of fibrin monomer. This monomer has the automatic capability of polymerizing with other fibrin monomer molecules, forming long fibrin threads within seconds. Unlike other tissue adhesive and hemostatic agents which rely on fibrinogen, the present invention makes use of the fibrin monomer, a totally separate molecule.

In the early stages of this polymerization, the fibrin monomer molecules attach to each other by loose hydrogen and hydrophobic bonds which can be broken apart with ease. It is at this point that the fibrin monomer may be utilized. However, under normal conditions, the blood plasma of vertebrates contains the inactive precursor of an enzyme, factor XIII, which can stabilize or strengthen the fibrin gels by introducing covalent bonds between the monomers. Activated Factor XIII binds neighboring molecules by covalently joining the side chains of certain glutamine acceptors. As a result of this cross-linking, stabilized fibrin has somewhat different properties than fibrin monomers.

As the present invention employs fibrin monomer, as opposed to fibrinogen, which all other tissue adhesives and hemostatic agents employ, the problems inherent in a fibrinogen system are eliminated. The problems in using fibrinogen, in a lyophilized formula, include the formation of a fibrin gel in the solution prior to lyophyllization because of the presence of thrombin. Thus lyophilizing a solution containing fibrin monomer instead of its precursor, fibrinogen, provides a solution to the problem of a single agent tissue adhesive, hemostatic agent. This solution lyophilizes to yield a truly homogeneous powder. When exposed to blood, thrombin activation of Factor XIII will precipitate the dissolved fibrin monomer as insoluble fibrin. The added thrombin also induces platelet aggregation which assists in achieving hemostasis.

The way in which fibrin monomer is derived from the thrombin-fibrinogen polymerization reaction and prevented from stabilizing is done at a point in which the fibrin monomer is easily disrupted during the reaction.

Lyophilized fibrinogen and thrombin are combined in a water solution. The fibrinogen is first dissolved at room temperature in distilled water and then subjected to sonication. Thrombin was then reconstituted, per directions. After dissolution, thrombin solution is injected into the fibrinogen solution.

Polymerization ensues instantaneously to form a soft gel. At this point the fibrin monomers are loosely bound and can be disrupted easily. To accomplish this disruption, a 10% ammonium hydroxide solution is added to the above solution, and the mixture is then sonicated or agitated until the gel is dissolved. The resultant fibrin monomer solution is then ready to be mixed into a final solution containing both thrombin and calcium chloride. This allows the solution to be lyophilized from a single solution containing all of its constituents, including thrombin. The agent is thus composed of fibrin monomer, thrombin, and calcium chloride; while it is assumed that sufficient factor XIII is present in the blood being lost at the site of injury.

The present invention relies on the presence of Factor XIII in the patient's own blood. When exposed to Factor XIII, the lyophilized fibrin monomer combination will precipitate as insoluble fibrin. The present invention therefore provides for a blood activated system employed as a powder without the premixing of ingredients.

What is claimed is:

1. A single agent hemostatic tissue adhesive comprising a lyophilized powder of fibrin monomer from human recombinant fibrinogen, calcium chloride, and bovine thrombin.

2. The invention of claim 1 whereto said hemostatic tissue adhesive does not require preparation, additives, or time, prior to use.

3. The invention of claim 1 consisting essentially of a lyophilized powder of fibrin monomer from human recombinant fibrinogen, calcium chloride, and bovine thrombin.

4. The invention of claim 1 wherein said fibrin monomer is from a human recombinant fibrinogen source free of virus.

5. A method of eliminating the risk of immunologic reaction to fibrinogen comprising applying the composition of claim 4 to injured tissue.

6. A method of eliminating the risk of immunologic reaction to fibrinogen comprising applying the composition of claim 1 to injured tissue.

7. A method of using a hemostatic tissue adhesive comprising using the invention of claim 1 with gauze, sponges, or other wound dressings in combination.

* * * * *